(12) United States Patent
Kurokawa et al.

(10) Patent No.: US 9,903,838 B2
(45) Date of Patent: Feb. 27, 2018

(54) EDDY CURRENT TESTING PROBE AND EDDY CURRENT TESTING METHOD

(71) Applicant: MITSUBISHI HEAVY INDUSTRIES, LTD., Tokyo (JP)

(72) Inventors: Masaaki Kurokawa, Tokyo (JP); Tomonori Shichida, Tokyo (JP)

(73) Assignee: MITSUBiSHI HEAVY INDUSTRIES, LTD., Tokyo (JP)

( * ) Notice: Subject to any disclaimer, the term of this patent is extended or adjusted under 35 U.S.C. 154(b) by 67 days.

(21) Appl. No.: 14/179,225

(22) Filed: Feb. 12, 2014

(65) Prior Publication Data

US 2015/0108970 A1     Apr. 23, 2015

(30) Foreign Application Priority Data

Oct. 22, 2013  (JP) .................................. 2013-219139

(51) Int. Cl.
    G01N 27/90         (2006.01)

(52) U.S. Cl.
    CPC ....... G01N 27/904 (2013.01); *G01N 27/9013* (2013.01)

(58) Field of Classification Search
    CPC ........... G01N 27/9013; G01N 27/9033; G01N 27/904
    See application file for complete search history.

(56) References Cited

U.S. PATENT DOCUMENTS

| 4,107,605 A | * | 8/1978 | Hudgell ............. G01N 27/9033 324/220 |
| 5,898,302 A | * | 4/1999 | Soules ................... G01N 27/72 324/209 |
| 6,018,242 A |   | 1/2000 | Piriou et al. |

(Continued)

FOREIGN PATENT DOCUMENTS

| DE | 102010048917 A1 | 4/2012 |
| EP | 2037261 A1 | 3/2009 |

(Continued)

OTHER PUBLICATIONS

Extended European Search Report dated Apr. 29, 2014, issued in corresponding European Patent Application No. 14155115.0 (8 pages).

(Continued)

*Primary Examiner* — Huy Q Phan
*Assistant Examiner* — Adam Clarke
(74) *Attorney, Agent, or Firm* — Westerman, Hattori, Daniels & Adrian, LLP (57) ABSTRACT

An eddy current testing probe includes: exciter coils 2 including a first exciter coil 2a and a second exciter coil 2b identical with each other and arranged in point symmetry, and each of which generates an alternating magnetic field to generate an eddy current in a test object; and detector coils 1 including a first detector coil 1a and a second detector coil 1b identical with each other, arranged in point symmetry, arranged in phase, and differentially connected to each other.

(Continued)

The exciter coils 2 and the detector coils 1 are arranged on a single plane. A center of symmetry O on a center line of symmetry CL2 of the coils 2*a*, 2*b*, is identical with a center of symmetry O on a center line of symmetry CL1 of the coils 1*a*, 1*b*, and the CL1 intersects with the CL2 at a right angle.

5 Claims, 11 Drawing Sheets

(56) References Cited

U.S. PATENT DOCUMENTS

| | | | | |
|---|---|---|---|---|
| 6,291,992 | B1* | 9/2001 | van Andel et al. | 324/240 |
| 6,339,327 | B1 | 1/2002 | Potiquet et al. | |
| 6,501,267 | B1 | 12/2002 | Kurokawa et al. | |
| 6,636,037 | B1* | 10/2003 | Ou-Yang | G01N 27/902 |
| | | | | 324/232 |
| 8,013,600 | B1* | 9/2011 | Yepez, III | G01N 27/9033 |
| | | | | 324/240 |
| 8,816,680 | B2* | 8/2014 | LePage | 324/239 |
| 2004/0232911 | A1* | 11/2004 | Schlicker | G01N 27/82 |
| | | | | 324/242 |
| 2005/0007108 | A1* | 1/2005 | Dogaru | G01N 27/904 |
| | | | | 324/235 |
| 2010/0139081 | A1* | 6/2010 | Decitre et al. | 29/595 |
| 2010/0312494 | A1* | 12/2010 | Korukonda | G01N 27/9046 |
| | | | | 702/38 |
| 2016/0209440 | A1* | 7/2016 | Ricotti | G01P 15/105 |

FOREIGN PATENT DOCUMENTS

| | | |
|---|---|---|
| EP | 2199785 A1 | 6/2010 |
| EP | 2642282 A1 | 9/2013 |
| JP | 59-10846 A | 1/1984 |
| JP | 10-104204 A | 4/1998 |
| JP | 3343860 B2 | 11/2002 |
| JP | 2010-117370 A | 5/2010 |
| JP | 2013-242223 A | 12/2013 |

OTHER PUBLICATIONS

Office Action dated Feb. 18, 2015, issued in corresponding Japanese Patent Application No. 2013-219139, with English translation (7 pages).

* cited by examiner

EDDY CURRENT TESTING PROBE AND EDDY CURRENT TESTING METHOD

BACKGROUND OF THE INVENTION

Field of the Invention

The present invention relates to a probe used for eddy current testing used for non-destructive testing.

Description of the Related Art

As a non-destructive testing method for metals, an Eddy Current Testing (ECT) is known. In this flaw detection method, an eddy current is generated on a surface of a test object by an exciter coil, and changes in a voltage (or changes in an impedance) of a detector coil caused by the influence of this eddy current are observed to detect a flaw developed in the test object.

The present inventors have proposed an eddy current testing probe that can accurately detect a flaw, in Japanese Patent No. 3343860. The eddy current testing probe of Japanese Patent No. 3343860 has an advantage of accurately detecting a flaw on a specimen based on a voltage difference generated between detector coils resulting from magnetic fluxes, even if a diagonal lift-off change occurs, which is a difference between distances from the detector coils to the test object.

In the eddy current testing probe of Japanese Patent No. 3343860, an exciter coil is arranged over the detector coils. In addition, there is distinction between up and down assuming that the test object is placed under the detector coil. Therefore, the eddy current testing probe of Japanese Patent No. 3343860 has a thickness of those of the detector coils and the exciter coil, and the probe may not be used in very narrow places.

The present invention is made based on such a technical problem, and has an object to provide an eddy current testing probe that can have a small thickness while having detector coils and exciter coils.

SUMMARY OF THE INVENTION

In order to achieve the above object, an eddy current testing probe of the present invention includes: exciter coils including a first exciter coil and a second exciter coil which are identical with each other and arranged in point symmetry, and each of which generates an alternating magnetic field to generate an eddy current in a test object; and detector coils including a first detector coil and a second detector coil which are identical with each other, arranged in point symmetry, and differentially connected to each other.

In the eddy current testing probe of the present invention, the exciter coils and the detector coils are arranged on a single surface.

Further, the exciter coils and the detector coils are arranged with a first center line of symmetry of the first detector coil and the second detector coil intersecting with a second center line of symmetry of the first exciter coil and the second exciter coil.

Since the exciter coils and the detector coils are arranged on a single surface, typically on a single plane, the eddy current testing probe of the present invention has a small thickness, and allows for performing eddy current testing even in narrow spaces.

In the eddy current testing probe of the present invention, a first center of symmetry on the first center line of symmetry and a second center of symmetry on the second center line of symmetry can be identical or substantially identical with each other, as seen in a plane view of the single surface.

In the eddy current testing probe of the present invention, it is preferred that the first exciter coil and the second exciter coil, and the first detector coil and the second detector coil are each formed by a coil having a rectangle shape in a plane view, and the first detector coil, the second detector coil, the first exciter coil and the second exciter coil are arranged with the first center of symmetry and the second center of symmetry being identical with each other, and with the first center line of symmetry and the second center line of symmetry intersecting with each other at a right angle.

With this configuration, the eddy current testing probes can be arranged in a rectangle manner as a whole, and it is possible to arrange a plurality of probe units tightly without gaps between them.

Furthermore, in the eddy current testing probe of the present invention, a pair of the first detector coil and the second exciter coil, and a pair of the second detector coil and the first exciter coil can be arranged offset from each other. With this eddy current testing probe, a capability of detecting a shallow flaw can be enhanced.

In the eddy current testing probe of the present invention, the first exciter coil and the second exciter coil, and the first detector coil and the second detector coil are each formed by a coil having a rectangle shape in a plane view, and the first detector coil, the second detector coil, the first exciter coil, and the second exciter coil can be arranged with the first center of symmetry and the second center of symmetry being identical with each other, and with the first center line of symmetry and the second center line of symmetry intersecting with each other at an angle other than a right angle.

With the eddy current testing probe of the present invention, a direction of an eddy current obtained by combining eddy currents generated by the first exciter coil and the second exciter coil can be the same as a direction of the first center line of symmetry.

With this eddy current testing probe, flaw detection can be performed without making the eddy current testing probe inclined to a direction of a flaw.

The eddy current testing probe of the present invention can perform flaw detection by using only one probe unit formed by the exciter coils and the detector coils, and furthermore, can perform the flaw detection with a plurality of probe units arranged in a predetermined direction.

With this eddy current testing probe, flaw detection can be performed to a given area without moving the probe units.

According to the present invention, all of the first exciter coil, the second exciter coil, the first detector coil, and the second detector coil can be formed by identical coils, in a case of arranging the plurality of probe units.

With this configuration, a coil that has been made to function for excitation at a certain timing, can be made to function for detection at a next timing, and therefore the exciter coils provided in a arranging direction can be used as the detector coils, and the detector coils can be used as the exciter coils, while switching their functions alternately, which allows for enhancing a resolution of the test result.

The present invention provides a method for performing flaw detection to a test object by using the eddy current testing probes described above. This eddy current testing method includes: an eddy current generating step of providing AC currents to the first exciter coil and the second exciter coil to generate eddy currents in the test object; and a detecting step of detecting presence/absence of a flaw in the test object based on a voltage difference generated between the first detector coil and the second detector coil by the eddy currents.

With the eddy current testing method of the present invention, flaw detection can be performed also to a given area of the test object by using a single testing probe. In this case, the eddy current generating step and the detecting step are performed every time the testing probe is moved to a certain position.

With this eddy current testing method, it is possible to effectively perform the flaw detection to the given area, with the reduced cost of testing probe.

In the eddy current testing method of the present invention, when a testing probe including a plurality of probe units arranged in a predetermined direction is used, a flaw detection process may be performed in the order in which the plurality of probe units are arranged, and the flaw detection process includes: the eddy current generating step of providing AC currents to the first exciter coils and the second exciter coils to generate eddy currents in the test object; and the detecting step of detecting presence/absence of a flaw in the test object based on a voltage difference generated between the first detector coil and the second detector coil by the eddy currents.

In a case where a testing probe including a plurality of probe units arranged is used and all of the first exciter coils, the second exciter coils, the first detector coils, and the second detector coils are formed by identical coils, it is preferable to perform the flaw detection process according to the following steps.

That is, when a flaw detection process is performed with a following probe unit after performing a flaw detection process with a preceding probe unit, an exciter coil made to function for excitation in the precedent flaw detection process can be made to function for detection in the following flaw detection process, and further, a detector coil made to function for detection in the precedent flaw detection process can be made to function for excitation in the following flaw detection process.

With this eddy current testing method, resolution of a flaw detection result can be enhanced because a function of a coil is alternately switched in such a manner that a coil made to function as an exciter coil in a precedent flaw detection process is made to function as a detector coil in a following flaw detection process.

According to the present invention, since exciter coils and detector coils are arranged on a single surface, the eddy current testing probe has a small thickness, and allows for performing eddy current testing even in narrow spaces.

BRIEF DESCRIPTION OF THE DRAWINGS

FIG. 1 is a diagram showing a schematic configuration of an eddy current testing probe according to a first embodiment of the present invention, in which

FIG. 2 shows the eddy current testing probe according to the first embodiment, in which

FIG. 7 shows extracted detection signals when performing the flaw detection using the probe shown in FIG. 6, in which

DETAILED DESCRIPTION OF THE PREFERRED EMBODIMENTS

First Embodiment

The embodiments of the present invention will be described below with reference to the accompanying drawings.

An eddy current testing probe 10 of the present embodiment is used for detecting a flaw 51 present on a surface of a test object 50 that is positioned thereunder, while moving over the test object 50.

The configuration of the eddy current testing probe 10 will be described below.

The eddy current testing probe 10 includes, as shown in FIG. 1, detector coils 1, and exciter coils 2 for generating alternating magnetic fields to generate eddy currents EC near a surface of the test object 50.

The detector coils 1 include a pair of a first detector coil 1a and a second detector coil 1b. The first detector coil 1a and the second detector coil 1b are differentially connected to each other. For each detector coil 1, a wound coil is used that has a wire wound therearound and is formed in a rectangle shape, and the first detector coil 1a and the second detector coil 1b are identical coils having an identical electromagnetic property.

The pair of the first detector coil 1a and the second detector coil 1b in a differential connection are connected to a bridge circuit 4, and configured to cause the bridge circuit 4 to output a flaw signal that indicates detection of the flaw 51 when voltages generated in the first detector coil 1a and the second detector coil 1b are different.

Note that the first detector coil 1a and the second detector coil 1b are referred to as the detector coils 1 when they do not need to be distinguished from each other, and they are referred to as the first detector coil 1a and the second detector coil 1b when they need to be distinguished from each other. This also applies to the exciter coils 2.

The exciter coils 2 include a pair of the first exciter coil 2a and the second exciter coil 2b. The exciter coils 2 (2, 2a, and 2b) are connected to an oscillator 3 for providing AC currents to the exciter coils 2. For each exciter coil 2, a wound coil is used that has a wire wound therearound and is formed in a rectangle shape, as the detector coils 1, and the first exciter coil 2a and the second exciter coil 2b are identical coils having an identical electromagnetic property.

Note that, in the first embodiment, the detector coil 1 and the exciter coil 2 may have different electromagnetic properties.

Figure 1A:
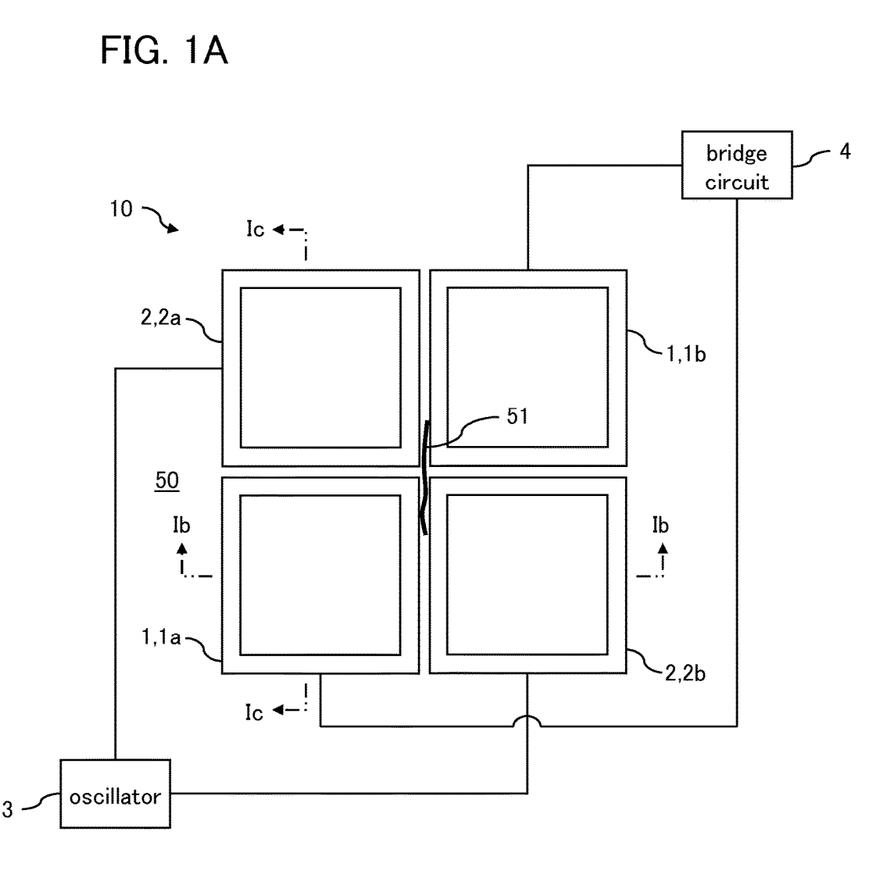
FIG. 1A is a plane view.
Figure 1B:
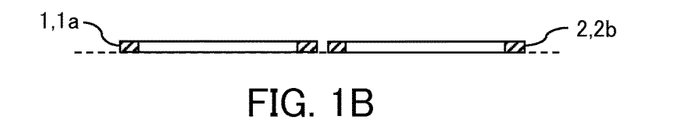
FIG. 1B is a cross-sectional view taken along a line Ib-Ib of FIG. 1A, and FIG. 1C a cross-sectional view taken along a line Ic-Ic of FIG. 1A.
Figure 1C:
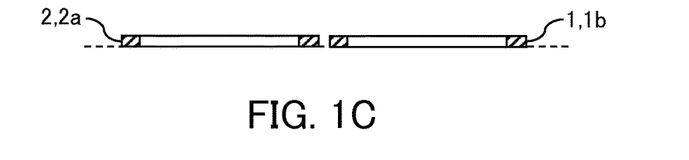

As shown in FIGS. 1B and 1C, the detector coils 1 (the first detector coil 1a and the second detector coil 1b) and the exciter coils 2 (the first exciter coil 2a and the second exciter coil 2b) are arranged on a single surface. Here, a typical example of the single surface is shown, where the detector coils 1 and the exciter coils 2 are arranged on a single plane.

Note that there are gaps between the first detector coil 1a, the second detector coil 1b, the first exciter coil 2a, and the second exciter coil 2b in FIGS. 1A, 1B and 1C, but the four coils may be arranged without gaps if they are electrically insulated.

Figure 2A:
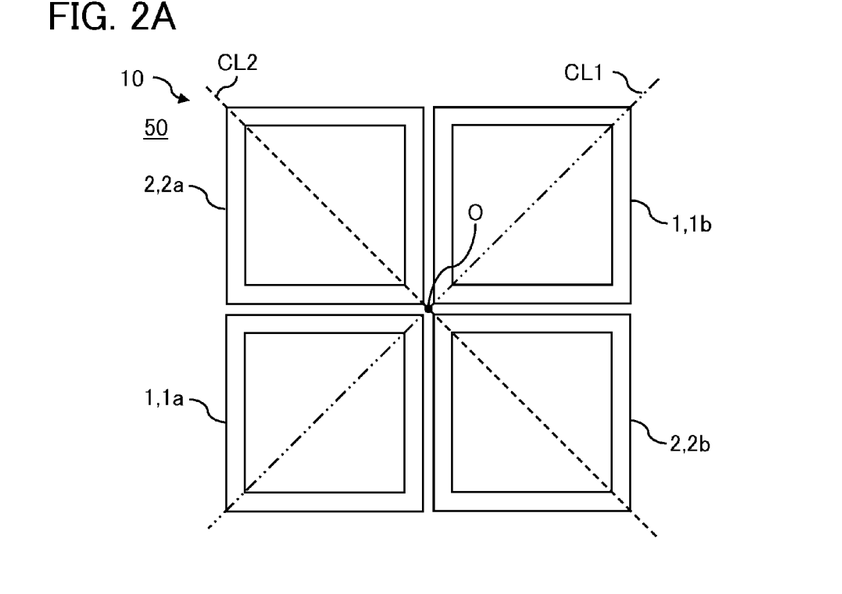
FIG. 2A is a diagram showing a positional relationship among detector coils and exciter coils, and FIGS. 2B and 2C each show how an eddy current is generated, where
Figure 2B:
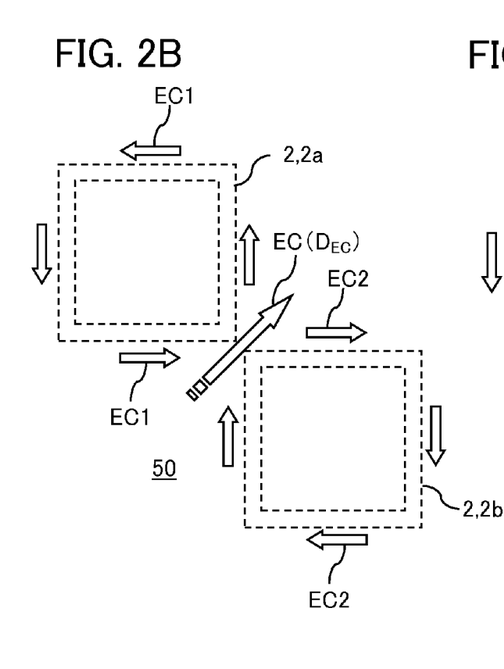
FIG. 2B shows a case where flaws are absent.

As shown in FIG. 2A, a pair of the first exciter coil 2a and the second exciter coil 2b are arranged in point symmetry. The first exciter coil 2a and the second exciter coil 2b each having a rectangle shape are arranged such that each vertex thereof directs to a center of symmetry (second center of symmetry) O. The exciter coils 2 are configured to generate a pair of eddy currents EC1 and EC2 that are adjacent to and symmetrical to each other as shown in FIG. 2B, by arranging the first exciter coil 2a and the second exciter coil 2b as described above, and in particular, the exciter coils 2 are configured to add these eddy currents EC1 and EC2 to generate a strong eddy current (composite eddy current) EC on a center line of symmetry CL2 of the first exciter coil 2a and the second exciter coil 2b that passes the center of symmetry O.

Figure 2C:
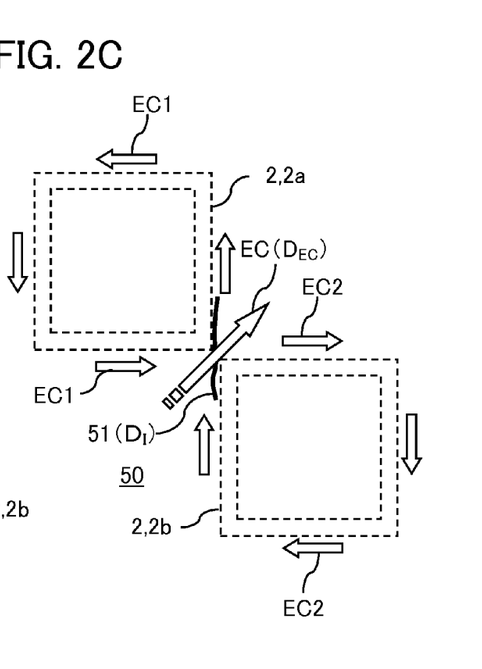
FIG. 2C shows a case where a flaw is present.

When the flaw detection is performed, the exciter coils 2 are arranged in such a direction that, as shown in FIG. 2C, a direction $D_{EC}$ of the eddy current EC is oblique with respect to a direction $D_I$ of the flaw 51 assumed in a case where the flaw is present on the surface of the test object 50, that is, such that the direction $D_I$ and the direction $D_{EC}$ intersect with each other. This is on a detection principal of the eddy current testing. That is, the eddy current testing probe 10 detects the flaw 51 by making use of changes in the eddy current EC caused by the flaw 51 that is on the surface of the test object 50, and serves as a disturbances of the eddy current EC, and if the direction $D_I$ of the flaw 51 is parallel to the direction $D_{EC}$ of the eddy current EC, the flaw hardly serves as a pronounced disturbance that acts on the eddy current EC. The direction $D_I$ of the flaw 51 on the surface of the test object 50 can be easily estimated based on manufacturing processes or the like of the test object 50.

As shown in FIG. 2A, the first detector coil 1a and the second detector coil 1b are arranged in point symmetry on a single plane so as to face to the test object 50 in parallel. The detector coils 1 are arranged together with the exciter coils 2 on the single plane.

The first detector coil 1a and the second detector coil 1b each having a rectangle shape are arranged such that each vertex thereof directs to the center of symmetry O. Note that, as shown in FIG. 2A, they are arranged such that a center line of symmetry CL1 passing the center of symmetry (first center of symmetry) O of the first detector coil 1a and the second detector coil 1b intersects with the center line of symmetry CL2 of the exciter coils 2 at the center of symmetry O in a plane view. Therefore, the detector coils 1 and the exciter coils 2 expand on the single plane, without overlapping with one another.

The eddy current EC is generated along the center line of symmetry CL1 of the detector coils 2 on the surface of the test object 50 in a plane view. In particular, since the eddy current EC is reliably generated around the center of symmetry O, and the center of symmetry O is also the center of symmetry O of the first detector coil 1a and the second detector coil 1b, the center of symmetry of the first detector coil 1a and the second detector coil 1b is positioned at a spot where the eddy current EC is most reliably generated.

Note that, a most preferred configuration is that in which the center line of symmetry CL1 of the detector coils 1 and the center line of symmetry CL2 of the exciter coils 2 intersect with each other at right angles at the center of symmetry O of both the center lines, but both the center lines of symmetry may not need to intersect with each other at right angles as long as they intersect with each other, and the centers of symmetry O of both the center lines may be only close together.

Next, there will be described an eddy current and flux linkage that are generated when currents (excitation current) are provided to the exciter coils 2 of the eddy current testing probe 10 configured as described above, with reference to FIG. 3.

Figure 3:
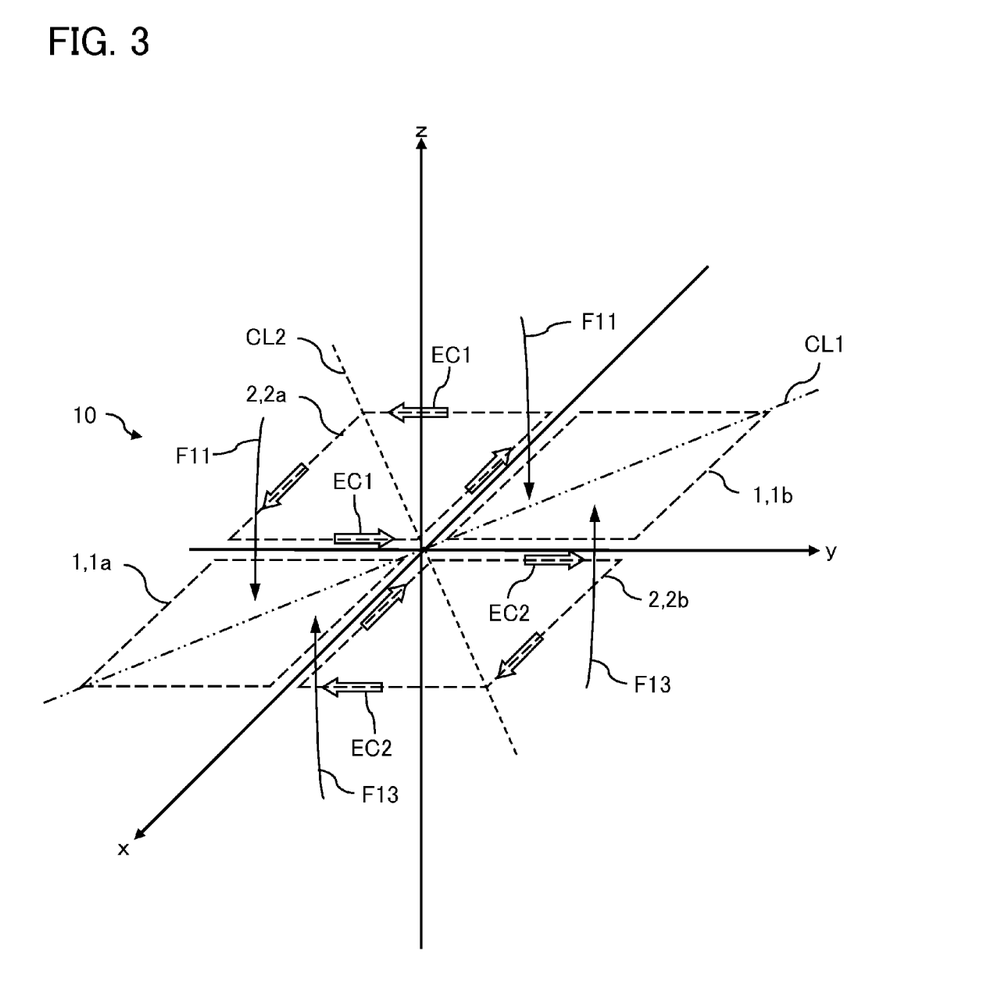
FIG. 3 is a diagram showing a positional relationship among eddy currents, flux linkages, the exciter coils, and the detector coils in the eddy current testing probe according to the first embodiment.

As shown in FIG. 3, when the excitation currents are provided to the exciter coils 2, a pair of eddy currents EC1 and EC2 are generated near surfaces of the first exciter coil 2a and the second exciter coil 2b, in addition, a downward flux linkage indicated by an arrow F11 is generated from the eddy current EC1, and an upward flux linkage indicated by an arrow F13 is generated from the eddy current EC2. Here, in a plane view, the detector coils 1 and the exciter coils 2 are arranged such that the centers of symmetry O thereof are identical with each other, and a direction of the first detector coil 1a and the second detector coil 1b (a direction of the center line of symmetry CL1) and a direction of the first exciter coil 2a and the second exciter coil 2b (a direction of the center line of symmetry CL2) intersect with each other at right angles. Therefore, the center of symmetry of the first detector coil 1a and the second detector coil 1b becomes identical with the center of symmetry of the eddy current EC as seen in a plane view, and the direction of the first detector coil 1a and the second detector coil 1b (the direction of the center line of symmetry CL1) becomes identical with a direction of the eddy current EC.

As a result, the downward flux linkage indicated by the arrow F11 and the upward flux linkage indicated by the arrow F13 act on the first detector coil 1a and the second detector coil 1b, respectively. That is, the flux linkages having opposite directions act on the first detector coil 1a and the second detector coil 1b, respectively.

Further, in a case where the flaw 51 is absent on the surface of the test object 50 (FIG. 2B), since no disturbance acts on the eddy currents EC1 and EC2, the flux linkages that act on the first detector coil 1a and the second detector coil 1b, respectively, are not different, and therefore voltages generated in the first detector coil 1a and the second detector coil 1b in response to these flux linkages are not different. Thus, a flaw signal is not generated from the bridge circuit 4.

On the other hand, in a case where the flaw 51 is present in the test object 50 (FIG. 2C), since a disturbance acts on the eddy currents EC1 and EC2, the flux linkages generated by the eddy currents EC1 and EC2 have a non-uniform distribution, which makes a difference in the addition of the flux linkages acting on the first detector coil 1a and the second detector coil 1b, and therefore a voltage difference occurs between the first detector coil 1a and the second detector coil 1b and this voltage difference causes the bridge circuit 4 to output a flaw signal.

We actually performed eddy current testing by using the eddy current testing probe 10, and the result of the testing was compared to the result of the flaw detection performed by a conventional eddy current testing probe (including a round exciter coil) described in Japanese Patent No. 3343860. As a result, we confirmed that the eddy current testing probe 10 had a flaw detection capability equivalent to the conventional eddy current testing probe.

As described above, since the detector coils 1 and the exciter coils 2 are arranged on the single plane, the eddy current testing probe 10 can have a thickness reduced by more than half compared with that of an eddy current testing probe in which a detector coil and an exciter coil are superposed. Therefore, the eddy current testing probe 10 allows for performing eddy current testing even in narrow spaces.

Figure 4A:
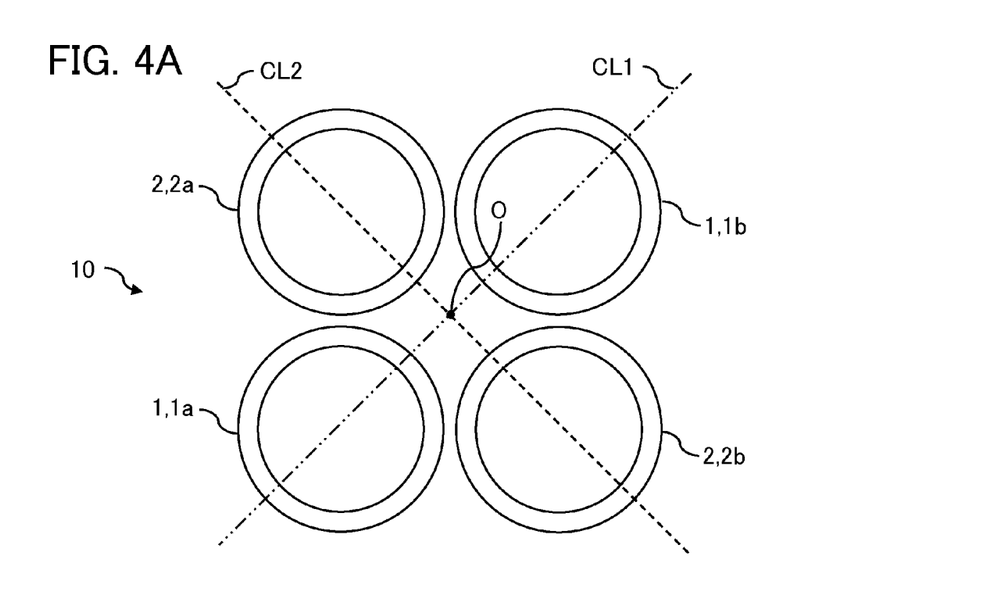
FIGS. 4A and B show a variation of the first embodiment.
Figure 4B:
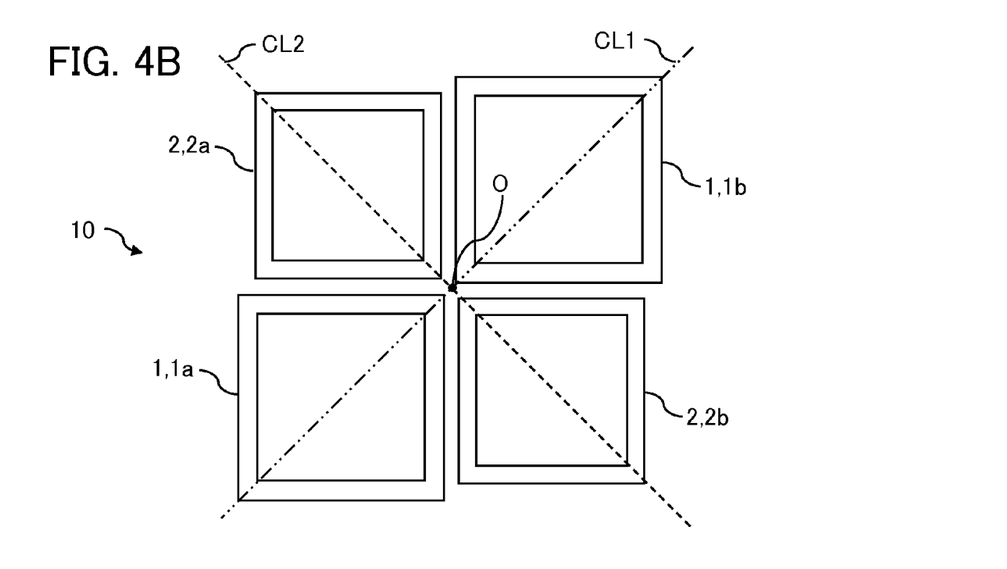

The above description shows the example in which the detector coils 1 and the exciter coils 2 each have a rectangle shape, but these coils can have any shape. For example, as shown in FIG. 4A, the detector coils 1 and the exciter coils 2 each having a toroidal shape can be used. In addition, as shown in FIG. 4B, the detector coils 1 and the exciter coils 2 may have magnetic properties different from each other, for example, may be sized differently.

The above description shows the example in which a flaw signal is generated by the bridge circuit 4, but the eddy current testing probe may be configured to include, for example, a voltmeter instead of the bridge circuit 4, and to detect the flaw 51 by monitoring a voltage difference between the first detector coil 1a and the second detector coil 1b by an operator using this voltmeter.

In addition, the example is shown in which eddy current testing is performed while the probe is moved along the surface of the test object 50, a plurality of sets of the eddy current testing probes 10 can be aligned to constitute a multi coil type eddy current testing probe, which can perform the flaw detection over a wide area at a time. In a second embodiment to be described next, a preferable example of the multi coil type eddy current testing probe using the present invention will be described.

Second Embodiment

An eddy current testing probe 20 according to a second embodiment relates to a multi coil type eddy current testing probe.

Figure 5:
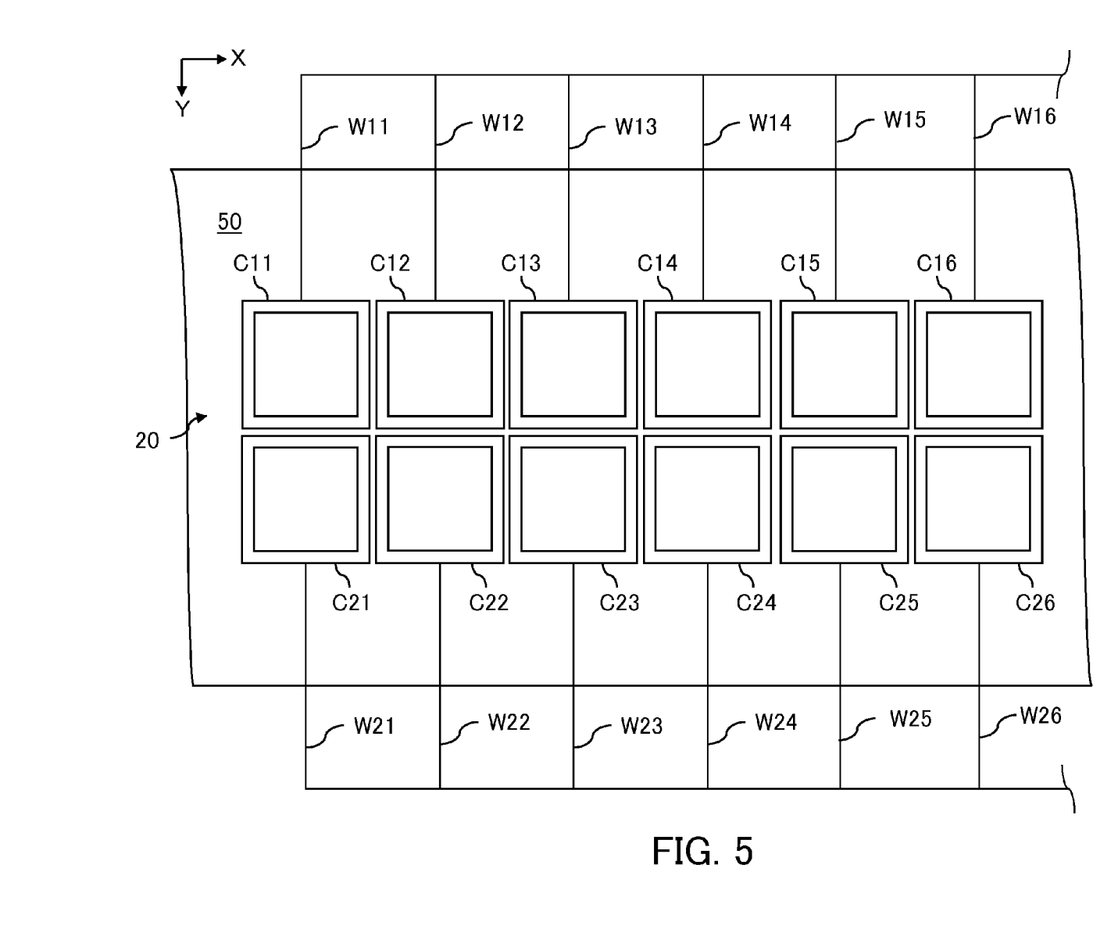
FIG. 5 is a plane view showing a schematic configuration of an eddy current testing probe according to a second embodiment of the present invention.

The eddy current testing probe 20 includes, as shown in FIG. 5, a total of 12 coils C arranged in a matrix pattern on a single plane, i.e., six coils C in a row direction X and two coils C in a column direction Y. Each coil C is made of, like the detector coils 1 and the exciter coils 2 in the first embodiment, a wound coil having a wire wound therearound. However, it is assumed that, in the second embodiment, all of the 12 coils C have an identical electromagnetic property. These coils C are denoted as C11, C12, C13, C14, C15, C16, C21, C22, C23, C24, C25, and C26, as shown in FIG. 5. However, they are collectively denoted as coils C when they do not need to be distinguished from one another.

Note that, the number of the coils C (i.e., 12) is only an example, and any number of the coils C can be provided in the row direction X and in the column direction Y. It should be understood that three coils C in the row direction X and two coils C in the column direction Y may be only provided to function as a multi-coil probe.

In the eddy current testing probe 20, four coils C provided in two rows and two columns constitute a minimum unit (probe unit) as a probe, and one unit of the probe constituted by the four coils C corresponds to the eddy current testing probe 10 in the first embodiment. However, in the eddy current testing probe 20, four of the coils C11, C12, C21, and C22 constitute one probe unit, and next, four of the coils C12, C13, C22, and C23 constitute one probe unit, and further, four of the coils C13, C14, C23, and C24 constitute one probe unit. In such a manner, in the eddy current testing probe 20, the adjacent four coils C form a probe unit.

In the second embodiment, the coils C11 to C26 do not have predetermined functions such as a detector coil and an exciter coil, like in the first embodiment, but any coil C can function as both the detector coil and the exciter coil. All of the coils C have, as a prerequisite, an identical electromagnetic property.

Wires W (W11 to W26) are connected to the coils C11 to C26, respectively. When the coils C function as exciter coils, excitation currents are provided to the coils C through the wires W, and when the coils C function as detector coils, a voltage difference between the coils C forming a pair is reflected to the corresponding wires W.

Next, an operation of the eddy current testing probe 20 on performing flaw detection to the test object 50 will be described with reference to FIG. 6 and FIG. 7.

The eddy current testing probe 20 uses coils C11, C12, C21, and C22 as a probe unit (first unit), at the beginning of the flaw detection (first timing of FIG. 6), wherein the coil C11 and the coil C22 are made to function as exciter coils while the coil C21 and coil C12 are made to function as detector coils. At this timing, AC currents are provided to the coil C11 and the coil C22, and a voltage difference between the coil C21 and the coil C12 is detected.

Figure 6:
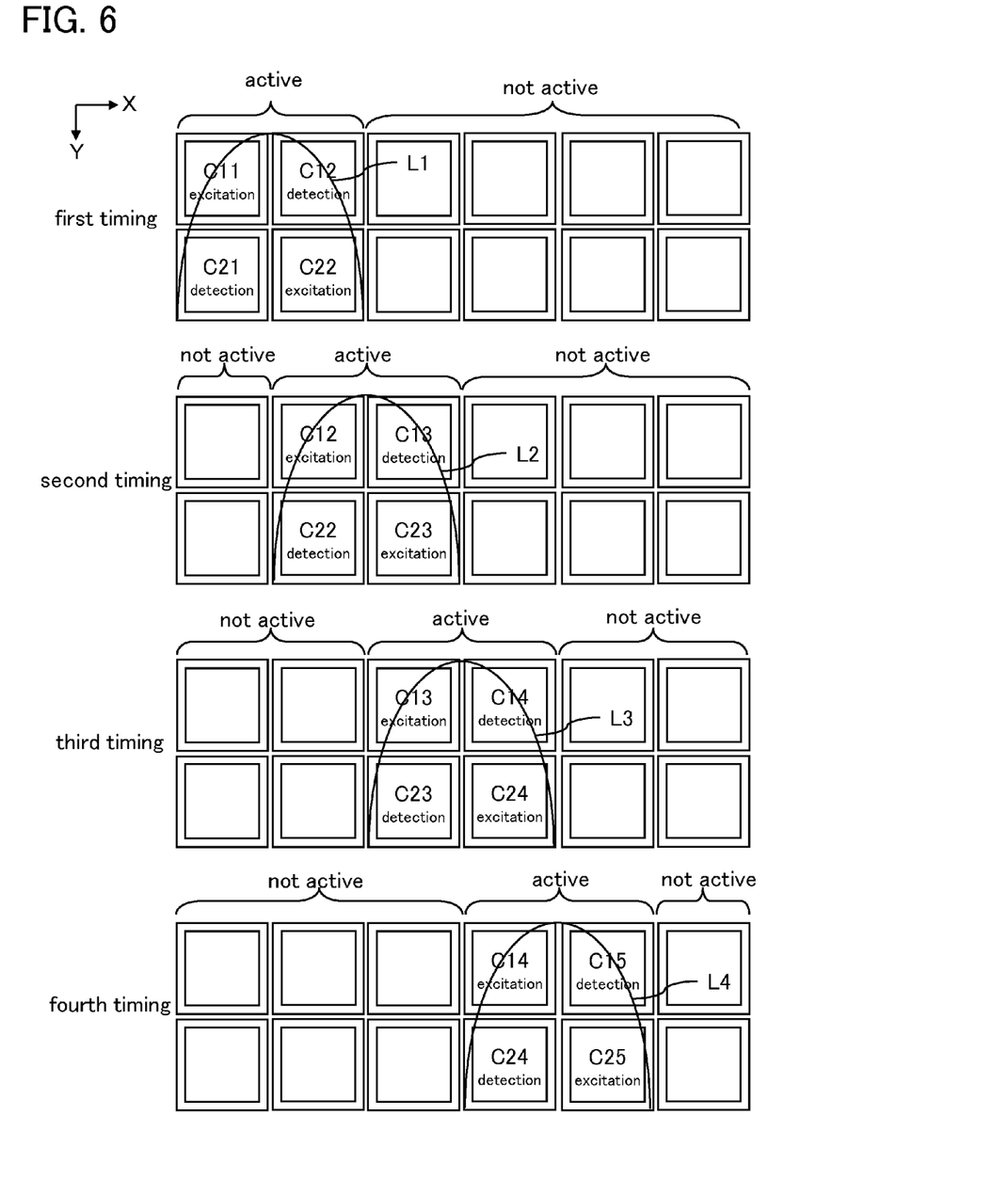
FIG. 6 is a diagram showing how to perform flaw detection using the eddy current testing probe according to the second embodiment.

After the flaw detection is performed by the first unit for a required period of time, the coils C constituting a probe unit (second unit) are switched to the coils C12, C13, C22, and C23 to perform the flaw detection (second timing of FIG. 6). At this timing, the coil C12 and the coil C23 are made to function as exciter coils, and the coil C22 and the coil C13 are made to function as detector coils. At this timing, AC currents are provided to the coil C13 and the coil C22, and a voltage difference between the coil C23 and the coil C12 is detected. Note that the coil C12 functions as a detector coil at the preceding first timing, and the coil C22 functions as an exciter coil at the preceding first timing.

At the next third timing, the coil C13 and the coil C24 function as exciter coils, and the coil C23 and the coil C14 function as detector coils. Further, at the next fourth timing, the coil C14 and the coil C25 function as exciter coils, and the coil C24 and the coil C15 function as detector coils.

Thereafter, the flaw detection process is performed in a longitudinal direction of the eddy current testing probe 20 while switching between coils C to form a probe unit, as described above.

Figure 7A:
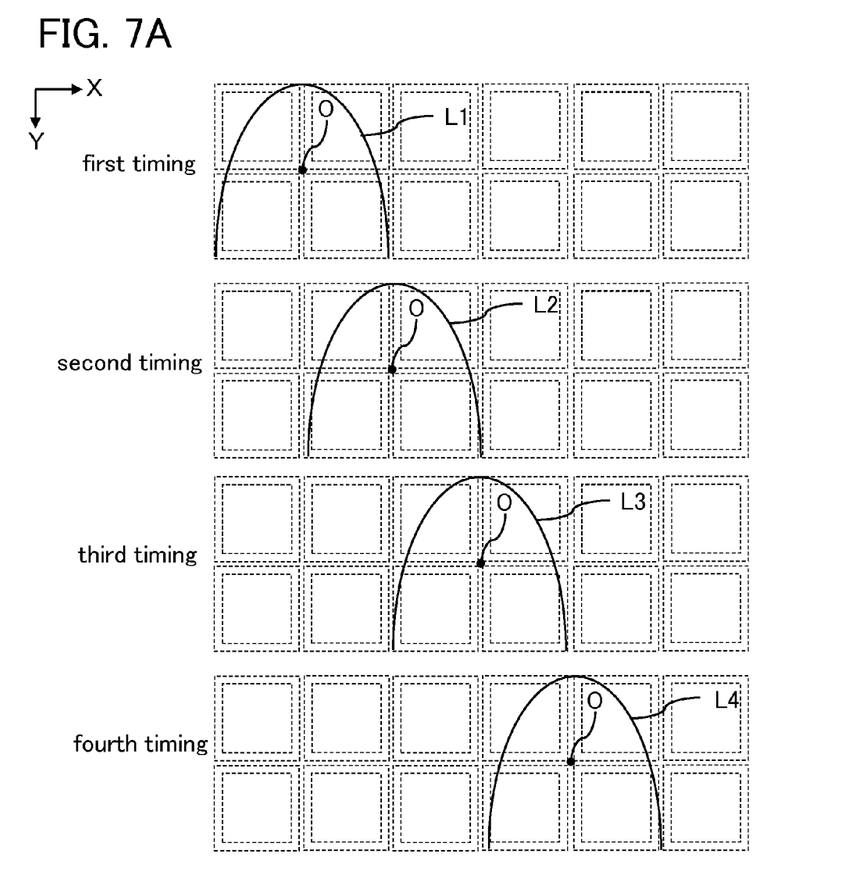
FIG. 7A shows the detection signals in a chronological order.

FIG. 7A shows detection sensitivity distributions at respective timings, which are superposed on the coils C, and it is understood that an area of the flaw detection shifts as a timing proceeds. Here, in FIG. 7A, an X axis denotes a distance from the center of the probe unit, and a Y axis denotes a signal amplitude (signal level) detected by a probe unit (first detector coil and second detector coil) when the flaw 51 is present at a position indicated by the horizontal axis. Curves L1, L2, L3, and L4 each denote a detection sensitivity distribution of each probe unit. The signal level reaches its peak when the flaw 51 is present at immediately under the center of symmetry O, and the detection sensitivity distribution curve L1 has its peak on the center line of symmetry CL1.

Figure 7B:
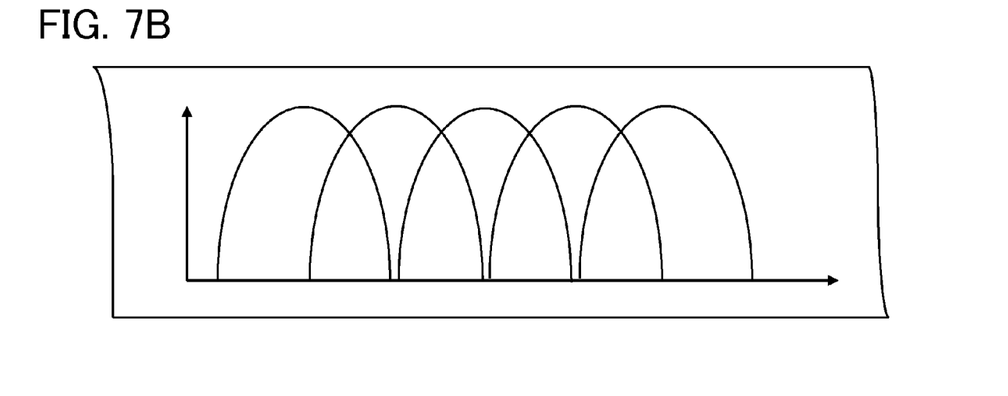
FIG. 7B shows the detection signals in a single row.

When detection sensitivity distributions at each timing are arranged in a single row, as shown in FIG. 7B, adjacent detection sensitivity distributions overlap with one another by ½ the period of the distribution, and therefore, the eddy current testing probe 20 can achieve a high detection sensitivity over the whole area in a flaw detection direction along the longitudinal direction of the eddy current testing probe 20.

As described above, since all of the coils C are arranged on the single plane in the eddy current testing probe 20, the eddy current testing can be performed even in a case where there is only a narrow space, like the first embodiment.

Further, in the eddy current testing probe 20, the rectangular coils C can be arranged in a matrix pattern, which allows the probe to be made tight.

Figure 8A:
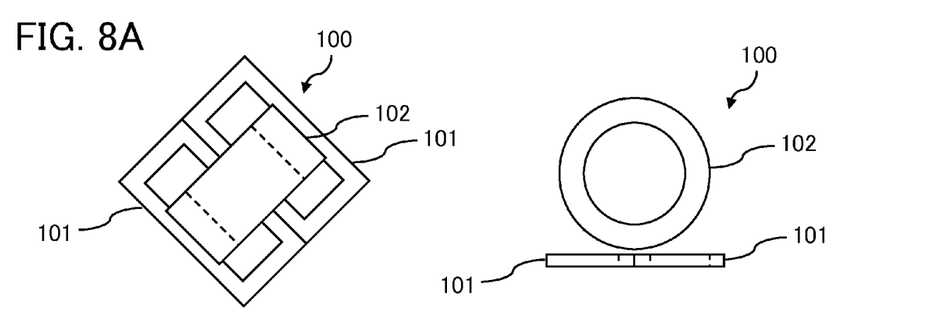
FIGS. 8A-C show a conventional eddy current testing probe described in Japanese Patent No. 3343860.

In contrast, an eddy current testing probe 100 disclosed in Japanese Patent No. 3343860 includes, as shown in FIG. 8A, an exciter coil 102 having a toroidal shape and a pair of detector coils 101 and 101, which are arranged in a vertical direction.

Figure 8B:
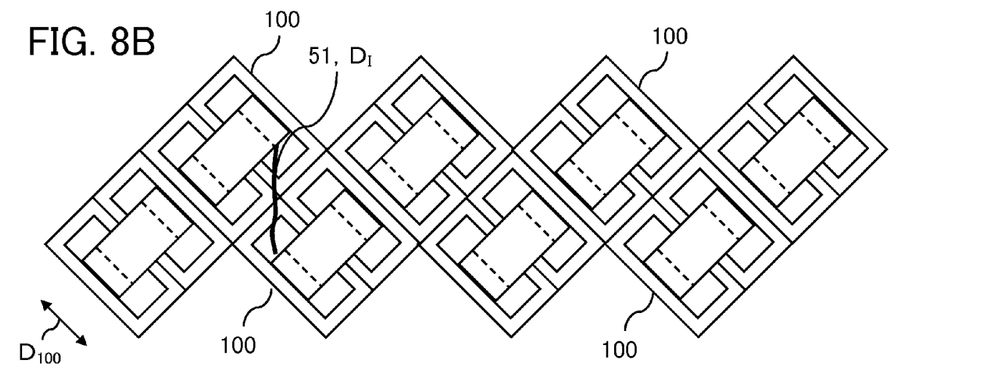
Figure 8C:
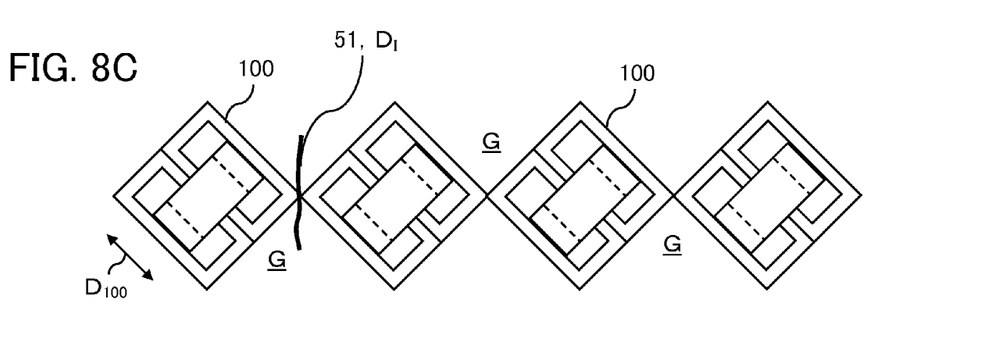

With the eddy current testing probe 100 of Japanese Patent No. 3343860, since a direction $D_{100}$ of the eddy current testing probe 100 needs to be made inclined to the direction $D_1$ of the flaw 51, when the plurality of eddy current testing probes 100 (probe units) are arranged only in one row, as shown in FIG. 8C, gaps G are made between adjacent probe units. Therefore, for the eddy current testing probe 100 of Japanese Patent No. 3343860, as shown in FIG. 8B, a plurality of probe units need to be arranged in two rows in order to perform the flaw detection to an area equivalent to that covered by the eddy current testing probe 20 in the second embodiment.

Therefore, the eddy current testing probe 20 according to the second embodiment can perform the flaw detection to a required area with a smaller number of the probe units as compared with Japanese Patent No. 3343860, and can give a higher resolution of a flaw detection result when comparing them in terms of an identical detection area.

Third Embodiment

Next, a third embodiment relates to an eddy current testing probe 30 that performs flaw detection in which a shallow flaw can be detected.

The present inventors have found that, with the eddy current testing probe 10 according to the first embodiment, the capability of detecting the flaw 51 passing a position of FIG. 1 may be lowered when the flaw 51 is present in a shallow position. Note that the position of FIG. 1 means a boundary portion between the first detector coil 1a and the second exciter coil 2b, and a boundary portion between the first exciter coil 2a and the second detector coil 1b, in the eddy current testing probe 10.

Figure 9A:
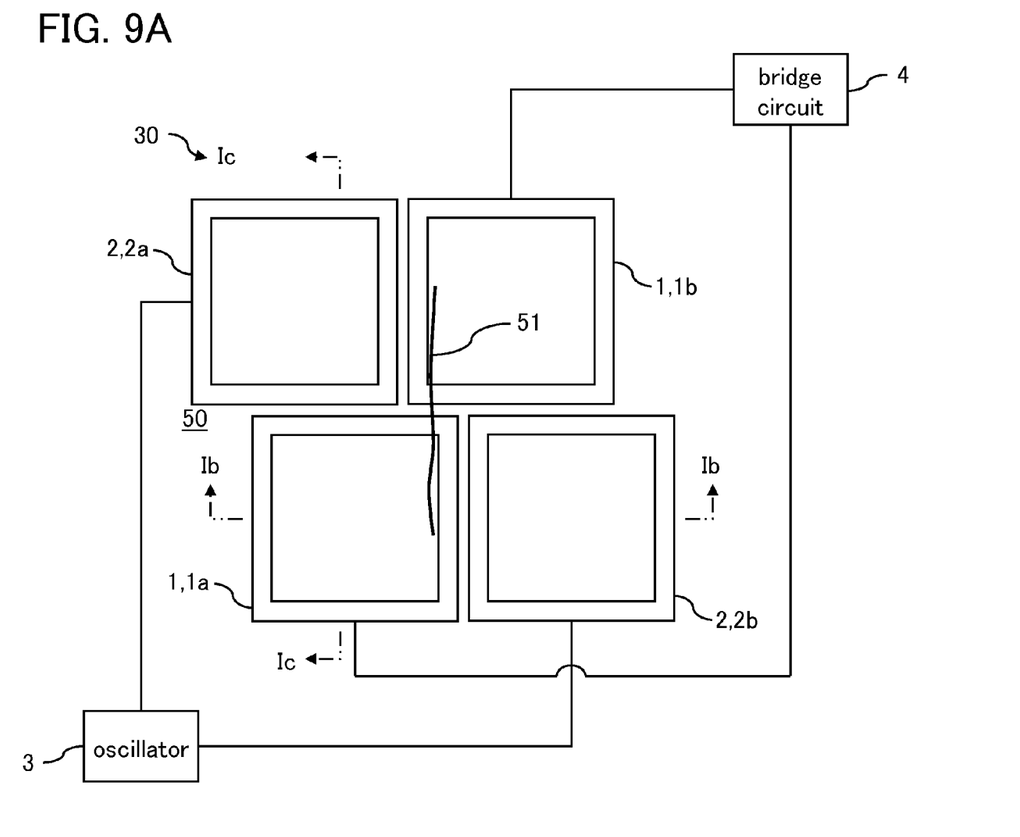
FIGS. 9A-C show a schematic configuration of an eddy current testing probe according to a third embodiment of the present invention.
Figure 9B:
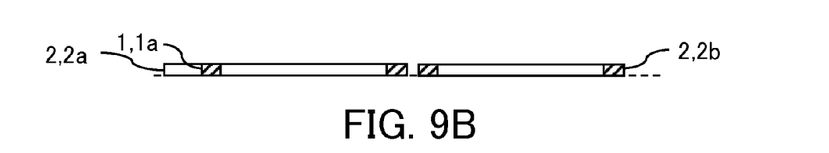
Figure 9C:
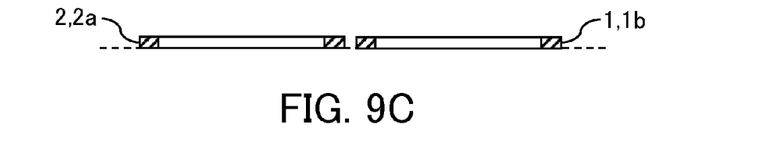

Thus, the present inventors have conducted studies and found that the eddy current testing probe 30 in which, as shown in FIG. 9, the pair of the first detector coil 1a and the second exciter coil 2b, and the pair of the first exciter coil 2a and the second detector coil 1b are arranged offset from each other, can detect the flaw 51, which is difficult to detect with the eddy current testing probe 10. In the eddy current testing probe 30, the first center of symmetry and the second center of symmetry are identical with each other, and the first center line of symmetry and the second center line of symmetry intersect with each other at angles other than right angles.

An amount of offset should be set depending on a member being a target of the flaw detection, a flaw, or the like, but it is set up to ½ the length of opposed sides of the first detector coil 1a and the first exciter coil 2a.

Although the preferable embodiments of the present invention are described above, the configuration described in the embodiments may be chosen or changed to other configurations without departing from the gist of the present invention.

For example, it is possible to constitute a multi coil type eddy current testing probe by arranging the eddy current testing probes 10 described in the first embodiment in one row, and to perform a flaw detection process using each eddy current testing probe 10 in turn.

Further, although the examples are described in which wound coils are used for the exciter coils and the detector coils, the present invention is not limited to this, and a coil formed in a film shape can be used therefor, for example.

Figure 10:
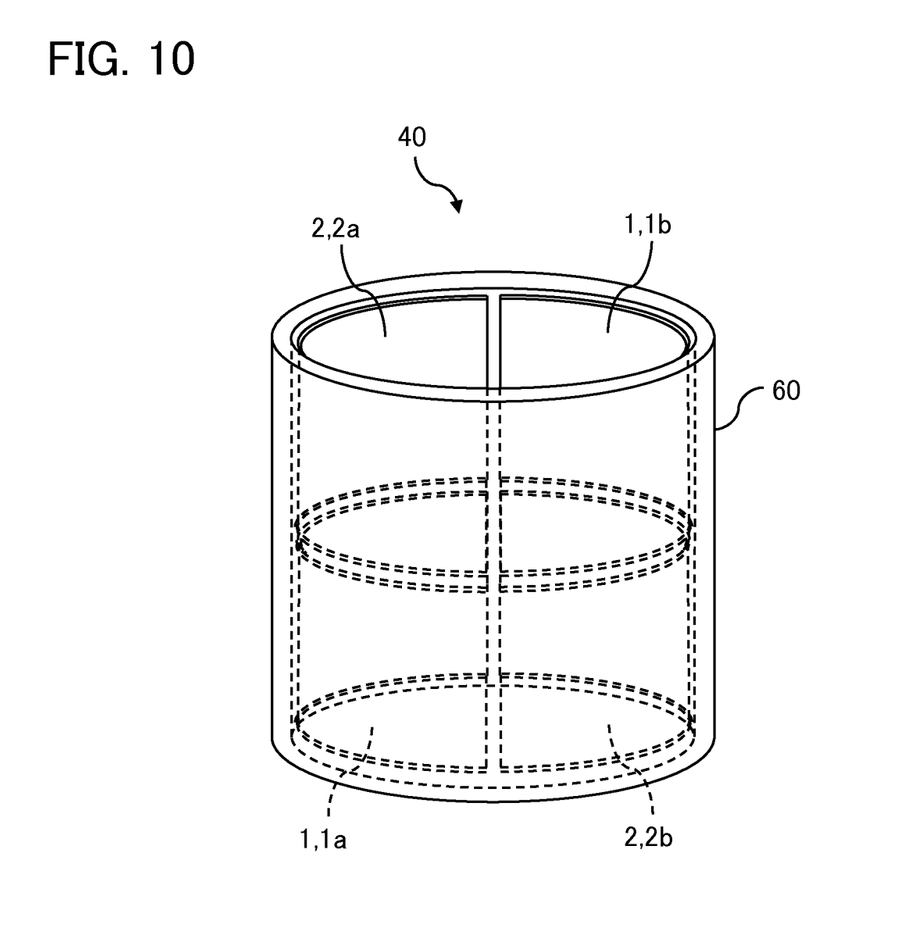
FIG. 10 is a diagram showing an example where the present invention is applied on a single cylindrical surface.
Figure 11:
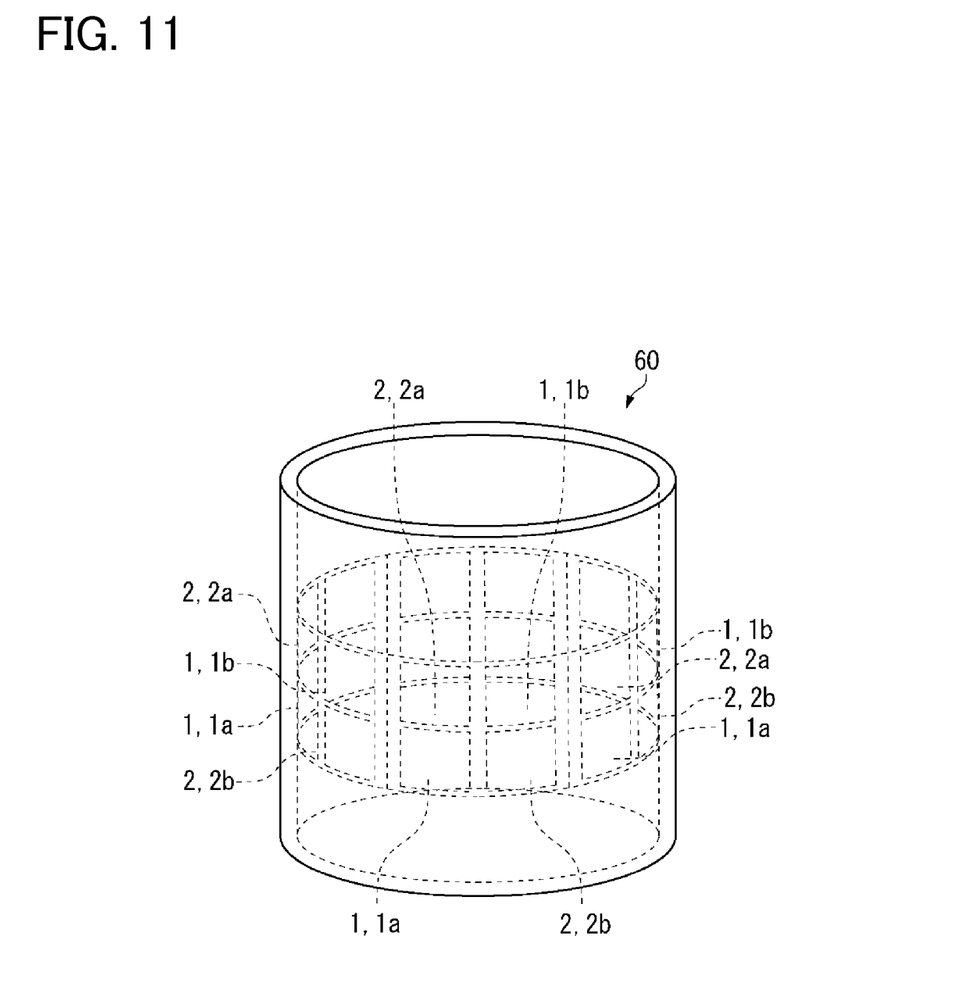
FIG. 11 is a diagram showing another example where the present invention is applied on a single cylindrical surface.

Still further, the first embodiment and the second embodiment show examples in which the coils are arranged on a single plane, but the present invention is not limited to a plane, for example, the coils may be arranged on a single curved surface. FIG. 10 shows this example, wherein an eddy current testing probe 40 includes a pair of detector coils 1 (first detector coil 1a and second detector coil 1b) and exciter coils 2 (first exciter coil 2a and the second exciter coil 2b) arranged on an inner peripheral surface of a cylindrical holder 60. Noted that a plurality of sets of the eddy current testing probes 40 shown in FIG. 10 can be aligned in the axial direction. Further, as shown in FIG. 11, the eddy current testing probe 40 may be configured to include a plurality of pairs of the detector coils 1 (first detector coil 1a and second detector coil 1b) and the exciter coils 2 (first exciter coil 2a and the second exciter coil 2b) arranged on the inner peripheral surface of the holder 60. Furthermore, the eddy current testing probe 40 may be configured to include a plurality of coils C having an identical electromagnetic property and each coil C capable of functioning as both the detector coil and the exciter coil arranged in a matrix pattern on the inner peripheral surface of the holder 60. These eddy current testing probes 40 do not only provide an advantage similar to the eddy current testing probe 10 described in the first embodiment and the eddy current testing probe 20 described in the second embodiment, but also can effectively perform flaw detection to the a test object having a cylindrical shape.

What is claimed is:

1. An eddy current testing probe comprising a plurality of probe units arranged in a predetermined direction, each probe unit comprising:
    exciter coils including a first exciter coil and a second exciter coil which are identical with each other and arranged in point symmetry, and each of which generates an alternating magnetic field to generate an eddy current in a test object; and
    detector coils including a first detector coil and a second detector coil which are identical with each other, arranged in point symmetry, and differentially connected to each other, wherein
    the exciter coils and the detector coils are arranged on a single surface without overlapping with one another, and
    the exciter coils and the detector coils are arranged with a first center line of symmetry of the first detector coil and the second detector coil intersecting with a second center line of symmetry of the first exciter coil and the second exciter coil at a right angle, and
    a first center of symmetry on the first center line of symmetry and a second center of symmetry on the second center line of symmetry are identical with each other, as seen in a plane view of the single surface,
    wherein a direction of an eddy current obtained by combining eddy currents generated by the first exciter coil and the second exciter coil is the same as a direction of the first center line of symmetry, and wherein the eddy currents generated by the first exciter coil and the second exciter coil are combined to generate an eddy current (EC ($D_{EC}$)) in the direction of the first center line of symmetry due to the arrangement of the first exciter coil and the second exciter coil which are identical with each other and arranged in point symmetry.

2. The eddy current testing probe according to claim 1, wherein the first exciter coil and the second exciter coil, and the first detector coil and the second detector coil are each formed by a coil having a rectangle shape in a plane view.

3. The eddy current testing probe according to claim 1, wherein all of the first exciter coil, the second exciter coil, the first detector coil, and the second detector coil are formed by identical coils.

4. An eddy current testing method for performing flaw detection to a test object by using the eddy current testing probe according to claim 1, wherein a flaw detection process is performed in an order in which the plurality of probe units are arranged, the flaw detection process including:

an eddy current generating step of providing AC currents to the first exciter coil and the second exciter coil to generate eddy currents in the test object; and a detecting step of detecting presence/absence of a flaw in the test object based on a voltage difference generated between the first detector coil and the second detector coil by the eddy currents.

5. The eddy current testing method according to claim 4, wherein all of the first exciter coil, the second exciter coil, the first detector coil, and the second detector coil are formed by identical coils, when the flaw detection process is performed with a following probe unit after performing the flaw detection process with a preceding probe unit, the exciter coil made to function for excitation in the precedent flaw detection process is made to function for detection in the following flaw detection process, and the detector coil made to function for detection in the precedent flaw detection process is made to function for excitation in the following flaw detection process.

\* \* \* \* \*